United States Patent [19]

Briody et al.

[11] Patent Number: 4,814,524

[45] Date of Patent: Mar. 21, 1989

[54] METHOD FOR CONVERTING ORGANIC CHLOROFORMATE TO THE CORRESPONDING ORGANIC CHLORIDE

[75] Inventors: Robert G. Briody, Clinton; James A. Manner, Akron, both of Ohio

[73] Assignee: PPG Industries, Inc., Pittsburgh, Pa.

[21] Appl. No.: 891,096

[22] Filed: Jul. 31, 1986

[51] Int. Cl.$^4$ .............................................. C07C 17/24
[52] U.S. Cl. .................................... 570/201; 568/606; 568/614; 568/610; 570/186; 570/218
[58] Field of Search ............... 570/201, 218, 261, 256, 570/186; 568/614, 606, 610

[56] References Cited

FOREIGN PATENT DOCUMENTS 2931777  2/1981  Fed. Rep. of Germany ...... 570/261

OTHER PUBLICATIONS

Clinch et al., Jour. Chem. Soc. B (1971) (4) 747–751.

*Primary Examiner*—Werren B. Lone
*Attorney, Agent, or Firm*—Irwin M. Stein

[57] ABSTRACT

Organic haloformate, e.g., chloroformate, compounds are converted to their corresponding halides, e.g., chlorides, by heating the haloformate, e.g., between 90° C. and 150° C., in the presence of a catalytic amount of an organic quaternary salt, e.g., quaternary ammonium or phosphonium salts, for a time sufficient to convert the haloformate to the corresponding halide.

19 Claims, No Drawings

METHOD FOR CONVERTING ORGANIC CHLOROFORMATE TO THE CORRESPONDING ORGANIC CHLORIDE

DESCRIPTION OF THE INVENTION

A variety of organic sulfonate compounds are used commercially as surfactants. One method that has been described for producing such surfactants involves the reaction of the chlorine-capped precursor compound with sodium sulfite. See, for example, U.S. Pat. No. 2,115,192. The chlorine capped precursor compound has been prepared by chlorinating the corresponding alcohol with phosphorus trichloride or thionyl chloride. When phosphorus trichloride is used as the chlorinating agent, difficulties in separating by-products, such as phosphorous acid, from the resulting principal chloride product are experienced. Thionyl chloride is economically unattractive as a chlorinating agent because it is a highly corrosive material. Moreover, it produces sulfur dioxide as a by-product of the chlorination reaction.

Phosgenation of alcohol precursors corresponding to the organic portion of the organic sulfonate surfactant and conversion of the resulting chloroformate to the chloride also can be used to prepare the chlorine capped precursor. However, converting the chloroformate to the corresponding chloride by a process which gives high yields of chloride product of acceptable color and minor amounts of by-products at reasonable cost has been difficult to achieve.

It has now been found that conversion of organic haloformates, e.g., chloroformates and bromoformates, to the corresponding halide compound, e.g., chloride and bromide, can be achieved readily and economically. In the process described hereinafter, organic haloformate is converted to the corresponding halide by heating the haloformate in the presence of a catalytic amount of a catalyst selected from the group consisting of organic quaternary ammonium and phosphonium salts for a time sufficient to achieve the foregoing conversion. In particular, the corresponding halide, e.g., chloride compound derived from the organic haloformate compound, especially organic chloroformate compounds useful as intermediates in the preparation of anionic surfactant materials, are obtained by heating the haloformate at between about 90° C. and 150° C. in the presence of a catalytic amount of the organic quaternary salt catalyst for between about 0.5 and 5 hours. Preferably, the conversion is performed in the substantial absence of water, e.g., under anhydrous conditions. Use of the aforedescribed process permits preparation of a product that has an acceptable color and that is at least about 95 weight percent, preferably at least 98 weight percent, of the corresponding halide. By-product carbon dioxide generated during decomposition of the chloroformate is also readily removed from the reaction medium and liquid reaction product as a gas.

DETAILED DESCRIPTION OF THE INVENTION

Organic quaternary salts that may be used in the process of the present invention may be represented, in one embodiment, by the general formula, $(Y_aH_{(4-a)}M)^+X^-$, wherein M is nitrogen or phosphorus, Y is the organic portion of the salt molecule bonded to M by covalent linkages, e.g., four independent monovalent aliphatic hydrocarbon groups, a is the number 4, and $X^-$ is a monovalent anion associated with the cation, $(Y_aH_{(4-a)}M)^+$.

The organic quaternary salts may be more graphically illustrated by the following formulae,

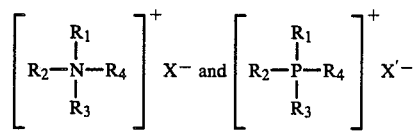

wherein $R_1$, $R_2$, $R_3$ and $R_4$ each are monovalent alkyl groups containing from 1 to about 25 carbon atoms, $X^-$ is a monovalent anion selected from the group consisting of halide ions, i.e., chloride, bromide or iodide, hydrogen sulfate anion ($HSO_4^-$) and the dihydrogen phosphate anion ($H_2PO_4^-$), and $X'^-$ is a halide ion, i.e., a chloride, bromide or iodide anion. The organic quaternary salts may also be depicted herein by the designation $(R_1R_2R_3R_4N)^+X^-$ or $(R_1R_2R_3R_4P)^+X^-$.

The number of carbon atoms in each of the alkyl substituents, $R_1$, $R_2$, $R_3$ and $R_4$ may vary considerably and may independently contain from 1 to about 25 or more carbon atoms. Preferably, each of the alkyl groups will contain from 1 to about 18 carbon atoms. In the case of alkyl groups of, for example, 8 or more carbon atoms, the number of carbon atoms in the group may be an average number, i.e., the hydrocarbon group contains a distribution of alkyl groups of varying carbon length.

The total carbon atom content of all of the groups, $R_1$, $R_2$, $R_3$ and $R_4$ will preferably be at least 12. The upper limit of the number of carbon atoms will depend on economic and other practical factors. An upper total limit of about 40 carbon atoms is a practical upper limit although quaternary compounds containing a total of 70 carbon atoms are contemplated. Generally, the total number of carbon atoms in the quaternary salt compound will be in the range of from about 12 to about 35 carbon atoms.

Of particular utility are organic quaternary salts which are alkyl trimethyl ammonium or phosphonium halides, dialkyl dimethyl ammonium or phosphonium halides, trialkyl methyl ammonium or phosphonium halides, and tetraalkyl ammonium or phosphonium halides wherein each of the alkyl groups contain from 8 to 18 carbon atoms and the halide is chloride, bromide, or iodide, preferably chloride or bromide. Of particular utility are those in which the alkyl groups are chosen from the group: butyl, octyl, decyl, dodecyl, tetradecyl ($C_{14}$), hexadecyl (cetyl) or octadecyl.

The catalytic amount of organic quaternary salt used in the present process should be soluble in the organic haloformate, e.g., chloroformate, be stable at the temperatures at which the reaction is carried out, and be devoid of functional groups that react in significant amounts with the organic haloformate starting material or resulting corresponding organic halide, e.g., chloride, at the conditions encountered during practice of the described process.

The organic quaternary salt is most preferably a liquid and is also soluble in or miscible with the resulting halide product. Hence, it may be left in the halide product and not separated therefrom. If the organic quaternary salt is a solid, it may be readily separated from the liquid reaction medium by any conventional liquid-solid separation technique, e.g., filtration. If it is an immiscible liquid, it may be separated by liquid-liquid separation techniques.

If the quaternary salt is miscible or soluble in the haloformate or halide product, it may be separated from the reaction medium by distilling off the halide product if the product has a boiling point of less than about 125°-150° C. at high vacuum. At higher temperatures, the quaternary salt used should be chosen so that its decomposition products are easily separated by distillation.

The amount of organic quaternary salt that is added to the organic haloformate to effect conversion to the corresponding halide may vary. Generally, reaction rates will increase with increasing amounts of the quaternary salt. Commonly, only that amount of the catalyst which is sufficient to catalyze the decomposition of the organic haloformate, e.g., chloroformate, to the corresponding halide, e.g., chloride, at satisfactory rates of reaction will be used, i.e., a catalytic amount. In particular, the amount of quaternary salt used as catalyst may be between about 0.05 and about 1.0 weight percent, e.g., between about 0.1 and about 0.3 weight percent, based on the weight of the organic haloformate reactant.

Examples of quaternary ammonium or phosphonium salts that may be used include: tetramethyl ammonium bromide, tetramethyl ammonium chloride, tetraethyl ammonium bromide, tetraethyl ammonium chloride, tetraethyl ammonium iodide, tetrapropyl ammonium bromide, tetrapropyl ammonium chloride, tetrapropyl ammonium iodide, triethylmethyl ammonium iodide, triethylpropyl ammonium iodide, tetrabutyl ammonium chloride, tetrabutyl ammonium bromide, tetrabutyl ammonium hydrogen sulfate, tributylmethyl ammonium iodide, tributylpropyl ammonium iodide, tetrahexyl ammonium bromide, tetrapentyl ammonium bromide, tetraisopentyl ammonium iodide, trioctylmethyl ammonium chloride, trioctylpropyl ammonium bromide, tetradecyl trimethyl ammonium bromide, trioctylpropyl ammonium bromide, cetyldimethylethyl bromide, cetyltrimethyl ammonium chloride, didodecyldimethyl ammonium bromide, tetraheptyl ammonium bromide, and tetrabutyl phosphonium chloride, and tetraethyl phosphonium bromide.

Other analogous organic quaternary salts may be similarly named by substituting another halide, i.e., chloride, bromide or iodide, for the halide specifically named in the aforesaid examples, and/or by substituting other alkyl groups containing from 1 to 25 carbon atoms for the alkyl groups specifically named. In addition, phosphonium compounds corresponding to the quaternary ammonium salts described above may also be used, i.e., phosphorus may be substituted for the nitrogen in the quaternary ammonium salts and vice versa. Such other quaternary ammonium or phosphonium salts are specifically contemplated herein although they are not specifically enumerated. Mixtures of one or more of the above-described organic quaternary salts may be used as the catalyst in the hereindescribed process.

Many of the organic quaternary ammonium salts are available commercially. The quaternary ammonium or phosphonium salts may be readily prepared by alkylation of the corresponding primary, secondary or tertiary amine or phosphine, in accordamce with the following general equation:

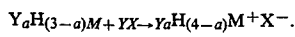

The alkylation reaction is usually conducted by warming (to 50°-100° C.) for a few hours or days stoichiometric amounts of the corresponding amine (or phosphine) with the appropriate alkyl halide, hydrogen sulfate or dihydrogen phosphate in a polar solvent such as methanol or acetonitrile.

Organic quaternary salts that are economically preferred for use in the practice of the present process include: tetrabutyl ammonium bromide, trioctyl methyl ammonium chloride and tetrabutyl ammonium hydrogen sulfate.

In accordance with the process of the present invention, the organic haloformate, e.g., chloroformate, compound is brought into contact with the organic quaternary salt catalyst and heated for a time sufficient to convert substantially all of the haloformate, e.g., chloroformate, compound to the corresponding halide, e.g., chloride. The process is preferably carried out in the absence of a solvent for the haloformate to eliminate solvolysis reactions. Preferably, the process is conducted in the substantial absence of water, i.e., under substantially anhydrous conditions since the haloformate is subject to hydrolysis with water to form a carbonate by-product which will reduce the yield of the halide product and contaminate the halide product.

The temperatures at which the aforesaid conversion occurs will vary depending on the organic haloformate compound; but, will typically be in the range of between about 90° C. and about 150° C., e.g., between about 100° C. and 120° C. The conversion may be accomplished at ambient pressures, although superatmospheric and subatmospheric pressures may be utilized. Heating of the organic haloformate compound is carried out for a time sufficient to convert substantially all, e.g., at least 95, preferably at least 98, and, most preferably, 100 weight percent of the haloformate to the corresponding halide. The time required to accomplish such substantial conversion will vary and depend on the haloformate compound employed, the amount and activity of the catalyst, and the temperatures used for the conversion. Generally, the higher the temperature used the shorter is the time required for the conversion reaction. Commonly, substantial conversion to the halide is accomplished in from about 0.5 to about 5 hours, e.g., between 1 and 3 hours.

If necessary, the liquid organic halide reaction product may be contacted with a suitable solid absorbant, e.g., activated carbon, alumina, or silica, to improve the color of the product by removing contaminating traces of colored impurities that may be formed in the reaction mixture as a consequence of the decomposition of the organic haloformate in the presence of the quaternary salt catalyst. Generally, the catalyst used in the present process will produce a halide product of acceptable color, i.e., one that has a color, as measured by the APHA (American Public Health Association) scale, of less than about 250, preferably less than 200 and more preferably less than 150. The color of the halide product produced by the process of the present invention may vary from colorless to yellow. Halide products produced using pyridine or an aromatic quaternary ammonium or phosphonium compounds have an unacceptable amber or dark brown color. The APHA color scale employs a visual comparison against a series of standard colors. The comparison may be made against standard solutions or by use of a color chart, as used in the Hellige Aqua Tester (Model 611-A) sold by Hellige, Inc. Lower conversion temperatures tend to reduce the color of the halide product, but require a longer conversion time.

The process of the present invention is applicable to organic haloformate compounds, particularly organic chloroformate and bromoformate compounds. The present process is particularly and advantageously utilized for the conversion of organic haloformate compounds that are used as precursors of organic sulfonates (and salts thereof, e.g., the sodium, potassium, and lithium salts) that have found application as surfactants and in related fields of application. Examples of organic haloformate compounds to which the process of the present invention can be applied are organic haloformates of the general formula:

$$R_5(OR''')_nOC(O)X$$

wherein X is halogen, e.g., chlorine and bromine, $R_5$ is selected from the group consisting of $C_1$-$C_{30}$ linear and branched alkyl, $C_5$-$C_6$ cycloalkyl, $C_1$-$C_4$ alkyl-substituted $C_5$-$C_6$ cycloalkyl, phenyl, alkyl substituted phenyl of the general formula, $(R_6)_bPh$-, wherein Ph is phenylene, $R_6$ is $C_1$-$C_{18}$ alkyl and b is an integer of from 1 to 3, phen($C_1$-$C_{18}$)alkyl, and $C_1$-$C_{18}$ alkyl-substituted phen($C_1$-$C_{18}$)alkyl having a total of from 7 to about 28 carbon atoms, R''' is the substituted ethylene group, —$CH_2$—$CH(R'''')$— wherein R'''' is selected from hydrogen, methyl and ethyl, and n is a number from 0 to 40. When R'''' is hydrogen, R''' is the ethylene group, —$CH_2$—$CH_2$—. When $R_5$ is phenyl or alkyl substituted phenyl, n is at least 1. Treatment of the foregoing organic haloformate, i.e., chloroformate, compounds in accordance with the process of the present invention results in the preparation of the corresponding halide, e.g., chloride, compound, i.e., compounds of the graphic formula, $$R_5(OR''')_nX$$

wherein $R_5$, R''', X and n are as defined hereinabove. These organic halide compounds can be readily converted to the corresponding sulfonates by reaction of the halide with an alkali metal sulfite, e.g., sodium, potassium, lithium, or ammonium sulfite, as disclosed in U.S. Pat. No. 2,115,192. The sulfonation reaction is typically conducted at between 150° C. and 170° C. and pressures of between about 60 psi (413.7 kPa) and 115 psi (792.9 kPa) for about 16 to 20 hours. See, for example, U.S. Pat. No. 4,329,268.

As described in the above general formula, $R_5$ may be a $C_1$-$C_{30}$ branched or linear chain alkyl. This alkyl group is commonly derived from primary and secondary alcohols. $R_5$ may be derived from a single alcohol or a mixture of alcohols that are themselves derived from natural fats and oils or petroleum fractions. The particular alkyl group used will depend on the ultimate application to which the sulfonate end product is intended. For example, the number of carbon atoms comprising $R_5$ may range from 1 to 30 carbon atoms, particularly 8 to 18 carbon atoms, e.g., from 11 or 12 to 15 carbon atoms. The mixture of alkyl groups in the alcohol precursor can vary and depends frequently on the particular manufacturer of the alcohol compounds from which the haloformate is derived.

The alkyl substituents of the alkyl substituted phenyl radicals will typically be a branched or straight chain hydrocarbon containing from 1 to 18 carbon atoms. The phenyl radical may contain from 1 to 3 of such alkyl substituents, more commonly 1 or 2 of such alkyl substituents. Similarly the phen($C_1$-$C_{18}$)alkyl and $C_1$-$C_{18}$ alkyl phen($C_1$-$C_{18}$)alkyl radicals will have from 1 to 18 carbon atoms in the alkyl portion(s) of the aforesaid radicals. With respect to the alkyl substituted phenalkyl radicals, the total number of carbon atoms in such radicals will commonly range from about 7 to 28 carbon atoms.

Alcohol precursor compounds containing polyoxyalkylene groups which comprise the organic haloformate are produced by reacting the corresponding alcohol with an alkylene oxide in the presence of a catalyst. The alkylene oxide can contain, for example from 2 to 4 carbon atoms and is the precursor of the substituted oxyethylene group, OR''', i.e., —$OCH_2$—$CH(R''')$—. More particularly, the alkylene oxide may be ethylene oxide, propylene oxide, or 1,2-butylene oxide. Also contemplated are compounds containing mixtures of alkylene oxide groups, e.g., mixtures of ethylene oxide and propylene oxide, and propylene oxide and butylene oxide. The number of alkyleneoxy groups present in the compound can vary from 1 to about 40, more typically, n will vary between about 2 and about 20, e.g., 3 to 15. The designation of the number of alkylene oxide units present per mole of the aforedescribed organic molecule, i.e., the letter "n", designates the average number of moles of alkylene oxide present per mole of organic molecule, e.g., ethoxylated alcohol chloroformate or chloride, and hence the value of n may be a fractional number between 1 and 40. Even though "n" is denoted as a number between 1 and 40, each organic molecule may contain a different number of alkylene oxide units with a distribution around the "n" value representing the average number of moles of alkylene oxide per mole of organic molecule. When n is 0, the haloformate compound contains no poly(alkylene oxide) groups.

Organic haloformate compounds described herein, e.g, organic chloroformates and bromoformates, may be prepared by reaction of the corresponding alcohol with the halogenating agents phosgene and bromophosgene (carbonyl bromide) respectively using techniques well known in the art for producing such materials, e.g, the chloroformates. The alcohol may be added to a pool of, for example, phosgene or the phosgene and alcohol added simultaneously to a reaction vessel. Preferably, the haloformate is the chloroformate.

Organic haloformate compounds described herein may be used as precursurs of derivative sulfonate compounds, many of which are used as surfactants. Examples of such sulfonate materials are the alkane and aralkyl sulfonates, the sulfonated polyoxyalkylene alkyl phenols and ethoxylated and sulfonated alcohols generally. In accordance with one embodiment of the present process, the corresponding alcohol is reacted with phosgene to prepare the corresponding chloroformate, i.e., $R_5(OR''')_nOC(O)Cl$, which is decomposed to the corresponding chloride, i.e., $R_5(OR''')_nCl$. This chloride compound may subsequently be reacted with an alkali metal sulfite, e.g., sodium sulfite, to form the corresponding sulfonate compound, i.e., $R_5(OR''')_nSO_3M$, wherein M is an alkali metal, e.g., sodium, lithium or potassium.

In accordance with a preferred embodiment of the present invention, liquid organic haloformate, e.g., chloroformate, compound is introduced into a nitrogen purged dry reaction vessel containing stirring means. About 0.25 weight percent of organic quaternary salt catalyst is also charged to the reaction vessel and the contents heated to between about 90° and 120° C. for about 1 to 3 hours. During the heating period, carbon dioxide is removed from the reaction vessel and forwarded to a scrubber and vent system to remove contaminants, e.g., hydrogen chloride and phosgene, which may not be discharged to the atmosphere. Accordingly, the scrubber system should contain chemical means for scrubbing out acidic materials. Carbon dioxide removed from the reaction vessel may be scrubbed from the vent gas by reaction with a suitable hydroxy compound, e.g., lime or barium hydroxide. The resulting liquid organic halide, e.g., chloride, reaction product may optionally be passed through a packed bed of alumina or carbon to remove color-producing impurities that may have been imparted to the reaction product during conversion of the haloformate.

In another embodiment of the present invention, it is contemplated that the catalytic amount of organic quaternary salt may be added to the alcohol precursor of the haloformate, i.e., the alcohol having the general formula, $R_5(OR''')_nOH$, wherein $R_5$, $R'''$ and n are as defined above, prior to conversion of the alcohol to the haloformate. Formation of the haloformate by simultaneous addition of, for example, phosgene and the corresponding precursor alcohol to the reaction vessel is performed at moderate temperatures, e.g., from about 23° C. to about 50° C. Following conversion of the alcohol to the haloformate, e.g., chloroformate, the reaction mixture is warmed to remove excess halogen reactant and by-product hydrogen halide, e.g., phosgene and hydrogen chloride, which are neutralized in appropriate scrubbers connected to the reaction vessel. Further warming of the haloformate in the presence of the quaternary salt to haloformate decomposition temperatures results in conversion of the haloformate to the corresponding halide. This technique allows preparation of the halogen-capped organic compound in one step using one reaction vessel. Such technique enhances removal of the halogen reactant and by-product hydrogen halide, e.g., phosgene and hydrogen chloride from the organic halide product, eliminates the loss of product resulting from transfers between vessels, and avoids isolation of the intermediate haloformate product, which may also result in the loss of product. A one step process also reduces the amount of equipment required to practice the process. In a modification of this embodiment, the quaternary salt is added to the haloformate product following its preparation and elimination of any residual halogen reactant, e.g., phosgene.

The process of the present invention is more particularly described in the following examples which are intended as illustrative only since numerous modifications and variations therein will be apparent to those skilled in the art.

EXAMPLE 1

A 1-liter flask was equipped with a stirrer, thermometer, Therm-O-Watch ® temperature controller, drying tube with calcium sulfate and heating mantle. The flask was dried and charged with 278.28 grams of a liquid chloroformate having the general formula, $R_5(OCH_2CH_2)_7OC(O)Cl$, wherein $R_5$ was an alkyl radical having an average of 13 to 14 carbon atoms. The reaction flask was then charged with 0.78 grams (0.28 weight %) of liquid trioctylmethyl ammonium chloride. Heat was applied to the reaction flask and gas evolution was observed to begin at a reaction mixture temperature of about 90° C. Heating of the reaction mixture continued with consequent gas evolution. When the temperature of the reaction mixture was 135° C., the reaction flask was removed from the heating mantle. The reaction temperature increased thereafter to about 141° C. and subsequently dropped to 133° C., at which point the reaction flask was placed back into the heating mantle. The temperature of the reaction mixture increased slowly to about 141°-142° C. After 90 minutes at a temperature of about 140° C., no further gas evolution was observed. The reaction mixture was permitted to cool down after a total reaction time of 2 hours at 140° C. Infrared analyses of the liquid reaction product indicated that no chloroformate was present, i.e., no peak was detected at 1780 cm$^{-1}$, and indicated the presence of only a small amount of carbonate impurity (transmittance at 1749 cm$^{-1}$ was of 97%). The reaction product was light yellow in color with an APHA value of approximately 185. The liquid reaction product was analyzed for total chloride by potentiometric titration after combustion in a Parr peroxide bomb. Total chloride found was 6.39 weight percent or 95.6% of the theoretical value of 6.68 weight percent.

EXAMPLE 2

Into a dry, 300 milliliter reaction flask equipped with a stirrer, thermometer, Therm-O-watch ® temperature controller, heating mantle, air condenser and drying tube, was placed 49.79 grams of 2-ethylhexyl chloroformate and 0.11 grams (0.22 weight percent) of trioctyl methyl ammonium chloride. The mixture was heated and gas evolution was observed to start at about 100°14 110° C. Heating was continued with the reaction temperature eventually reaching 145° C. Samples of the reaction mixture were removed after 15 minutes, 30 minutes, and 60 minutes - sample times being calculated from the point at which the reaction mixture reached 128° C. Gas chromatographic analyses of the samples indicated the presence of chloroformate (about 22 percent chloroformate in the one-hour sample). An additional 0.25 grams of trioctylmethyl ammonium chloride was added to the reaction flask and the contents heated to about 140° C. Gas evolution was again observed when the reaction mixture reached about 140° C. After an additional 1 hour at 140° C., the reaction mixture was cooled. The total amount of catalyst added was about 0.92 weight percent. Gas chromatographic analyses of the liquid reaction mixture indicated that it contained only about 0.07 percent 2-ethylhexyl chloroformate. Mass spectrometric analyses of the final reaction product showed that the product had a spectrum that matched the spectrum for 1-chloro-2-ethylhexane, i.e., the corresponding chloride product of 2-ethylhexyl chloroformate.

EXAMPLE 3

A dry 100 milliliter reaction flask equipped with a stirrer, thermometer, Therm-O-Watch ® temperature controller, heating mantle and drying tube was charged with 48.08 grams of a chloroformate having the general formula, $R_5(OCH_2CH_2)_3OC(O)Cl$, wherein $R_5$ is an alkyl group having an average of 13 to 14 carbon atoms, and 0.27 grams of tetrabutyl ammonium bromide. Heat was applied to the flask. At 90° C., a small amount of gas evolution was observed which increased significantly when the reaction mixture reached temperatures of 100°-110° C. Reaction temperatures increased to 155° C. at which time the liquid reaction mixture was cooled with a water bath to about 120° C. The reaction flask was placed back in the heating mantle and the temperature was held at about 140° C. for a total of two hours. Samples were removed at reaction times of 30 minutes, 1 hour, and 2 hours. Infrared analysis of the liquid reaction product indicated that no chloroformate was present in the 30 minute sample (no carbonyl peak at 1780 cm$^{-1}$), and only a small amount of carbonate by-product had been formed (93% transmittance at 1749 cm$^{-1}$).

EXAMPLE 4

A dry 100 milliliter flask equipped as in Example 3 was charged with 48.20 grams of the chloroformate of Example 3 and 0.23 grams of trioctylmethyl ammonium chloride. The flask was heated and gas evolution was observed at about 100°–110° C. The temperature of the reaction mixture in the flask attained a maximum temperature of 146° C. and thereafter was held at 140° C. Samples were removed from the reaction flask 30 minutes, 1 hour and 2 hours after the reaction mixture initially attained a temperature of 140° C. Infrared analysis of the liquid reaction product indicated that no chloroformate was present in the 30 minute sample (no carbonyl peak at 1780 cm$^{-1}$), and only a small amount of carbonate by-product had been formed (90% transmittance at 1749 cm$^{-1}$).

EXAMPLE 5

A dry 100 milliliter reaction flask equipped as in Example 3 was charged with 48.28 grams of the chloroformate described in Example 3 and 0.24 grams of trimethylhexadecylammonium bromide. The flask was heated and gas evolution observed at about 110° C. The reaction mixture attained a temperature of 146° C. and thereafter was held at about 140° C. Samples were removed from the reaction flask at 30 minutes, 1 hour and 2 hours after the reaction mixture initially attained a temperature of 140° C. Infrared analysis of the liquid reaction product indicated that no chloroformate was present in the 30 minute sample, and only a small amount of carbonate by-product had been formed (92% transmittance at 1749 cm$^{-1}$).

EXAMPLE 6

A dry 100 milliliter reaction flask equipped with stirrer, thermometer, Therm-O-Watch ® temperature controller, heating mantle, vent line and drying tube was charged with 0.24 grams of tetrabutyl ammonium dihydrogen phosphate and 49.89 grams of a liquid chloroformate having the general formula, $R_5(OCH_2CH_2)_7OC(O)Cl$, wherein $R_5$ is an alkyl group having an average of 13 to 14 carbon atoms. Heat was applied to the flask while stirring the contents. At 110° C., a few bubbles of gas were observed emanating from the liquid reaction medium. At 123° C., gas evolution increased significantly. Heating was continued until the contents of the reaction flask reached 140° C. The Therm-O-Watch ® controller was then set at 140° C. The reaction mixture was maintained at about 140° C. for 3.3 hours at which time it was cooled. Analysis of a sample of the reaction mixture by infrared analysis indicated that decomposition of the chloroformate was complete. A small amount of carbonate by-product was observed in the infrared scan.

EXAMPLE 7

A dry 100 milliliter reaction flask equipped with magnetic stirrer, thermometer, Therm-O-Watch ® temperature controller, heating mantle, vent line and drying tube was charged with 55.88 grams of a molten chloroformate having the general formula, $R_5(OCH_2CH_2)_{15}OC(O)Cl$, wherein $R_5$ is an alkyl group having an average of 13 to 14 carbon atoms, and 0.50 grams of tetrabutyl ammonium hydrogen sulfate. The reaction mixture was heated while stirring the contents. At 103° C., a few gas bubbles were observed. Gas evolution became significant at 124° C. and increased with increasing temperature. The Therm-O-Watch ® controller was set to hold the temperature of the reaction mixture at 140° C. After 3 hours at 140° C., no bubbles were visible in the reaction mixture. The contents of the flask were cooled and submitted for infrared analysis. No chloroformate was found in the product. A small amount of carbonate by-product was observed in the infrared scan.

EXAMPLE 8

A two-liter round bottom flask equipped with a stirrer, thermometer, Therm-O-Watch ® temperature controller, dry ice-acetone condenser and vent line connected to a scrubber was used as a reactor. An addition flask connected to the reactor with tubing having a small in-line pump was charged with 672 grams of an ethoxylated essentially linear alkanol in which the alkyl group was a mixture of linear primary $C_{12}$–$C_{15}$ alkyl groups and the average number of ethoxy groups was three, and 2.4 grams of tricaprylyl methyl ammonium chloride. A source of phosgene was also connected by means of a separate line to the reactor. Phosgene was charged slowly to the reactor until about 10 grams had been added. At that time, the alcohol/catalyst mixture was fed slowly to the reactor simultaneously with the phosgene- the rate of phosgene and alcohol addition being such so as to maintain an excess of phosgene in the reactor. The alcohol/catalyst mixture was added to the reactor over a period of about 2 hours and 10 minutes, phosgene addition being completed about 5 minutes sooner. The temperature of the reactor contents rose from about 24° C. to about 52° C. during this period. The reactor was air cooled.

A heating mantle was placed around the reactor flask and the contents heated from about 40° C. to 90° C. over a period of about 35 minutes. The temperature was then increased to 100° C. over 10 minutes, to 110° C. over an additional 40 minutes and to 120° C. over an additional 60 minutes. During the heat-up of the reactor contents, phosgene and hydrogen chloride evolved from the reactor. The reaction contents were maintained at 120° C. for about 2 hours and then cooled to room temperature (about 25° C.) in about 60 minutes. The reactor contents were left overnight at room temperature under slow agitation. The next morning the reaction product was degassed for one hour at 70° C. Infrared analysis of a sample of the product showed small peaks at 1780 cm$^{-1}$ and 1750 cm$^{-1}$, indicating small amounts of chloroformate and by-product carbonate. A chloride assay of a sample of the product was reported as 101.6 percent. The APHA color of the product was reported as about 250.

EXAMPLE 9

The general synthesis procedure of Example 8 was followed using as the alcohol an ethoxylated linear alcohol in which the alkyl group was a mixture of linear primary $C_{12}$–$C_{15}$ alkyl groups and the average number of ethoxy groups was fifteen. A total of 1079 grams of the alcohol was used. 3.5 grams of tricaprylyl methyl ammonium chloride was used to catalyze the conversion of the chloroformate to the chloride. The alcohol was added over a period of 1 hour and 40 minutes—the phosgene was added over a period of 1½ hours. The temperature of the reactor contents during formation of the chloroformate rose from 25° C. to 57° C.

At the completion of the phosgenation reaction, a heating mantle was placed around the reactor flask and the contents heated to 90° C. over 20 minutes. The temperature was then increased stepwise to 120° C. over 22 minutes and maintained at 120° C. for 5 hours. A yellow product was submitted for chloroformate and chloride assay, and acidity. No chloroformate or acidity was detected. The percent chloride was reported at 109.1%, 108.5% (two determinations).

EXAMPLE 10

The apparatus general synthesis procedure and ethoxylated alkanol described in Example 8 was used in this Example. 672 grams of the alkanol (without catalyst) was charged to the addition flask and reacted with phosgene in the reaction flask over a period of about 2¼ hours. The temperature of the reactor contents rose from about 24° C. to 50° C. during preparation of the chloroformate. Following completion of the phosgenation reaction, the reaction product was stirred for about one hour without applying any heat to the reaction flask.

2.4 grams of tricaprylyl methyl ammonium chloride was mixed with 10 grams of the corresponding ethoxylated alkanol chloride and the mixture added to the reaction product in the flask. The catalyst reaction product mixture was heated stepwise to 120° C. over a period of one hour by applying a heating mantle to the reaction flask. The temperature of the reactor was maintained at 120° C. for about 2¼ hours and then was allowed to cool overnight. In the morning, the reaction product was warmed to about 100° C., stirred and air degassed for 30 minutes. The reactor product had a yellow color. Infrared analysis indicated only a small amount of residual chloroformate and the formation of a small amount of by-product carbonate. A chloride assay of the product reported a total chloride of 99.8 percent.

While the process of the present invention has been exemplified by the use of certain alkyl chloroformates and ethoxylated alkyl chloroformates it is expected that similar results will be obtained with corresponding bromoformates. Similarly, while the process of the present invention has been exemplified with using certain organic quaternary salts, it is expected that similar results may be obtained with other organic quaternary salts—all as defined in the present specification.

EXAMPLE 11

A dry 100 milliliter three-necked flask was equipped with a magnetic stirring bar, air condenser, drying tube with calcium sulfate, heating mantle, thermometer, and Therm-O-Watch ® temperature controller was charged with 49.03 grams of 2-ethylhexyl chloroformate and 0.38 grams (0.77 weight percent) of tetrabutyl phosphonium bromide. The mixture was heated slowly with stirring and gas evolution was observed to start at 65° C. Heating was continued until the reaction mixture reached 140° C., at which time the flask was removed from the heating mantle and placed in a water bath to lower its temperature. When the temperature reached 111° C., gas evolution stopped and a sample of the reaction mixture was taken. The flask was replaced in the heating mantle, its temperature increased to 120° C., and maintained there for about 38 minutes. The flask was then removed from the heating mantle and cooled to room temperature. Gas chromatographic analyses of the aforesaid sample indicated the absence of 2-ethylhexyl chloroformate and the presence of 2-ethylhexyl chloride (98.7 area percent).

While the invention has been described in detail with respect to certain embodiments thereof, it is to be understood that the invention is not intended to be limited to such details except as and insofar as they appear in the appended claims.

We claim:

1. A method for preparing the corresponding halide of an organic haloformate of the general formula, $$R_5(OR''')_nOC(O)X$$

wherein X is a chlorine or bromine, $R_5$ is selected from the group consisting of $C_1$-$C_{30}$ alkyl, $C_5$-$C_6$ cycloalkyl, $C_1$-$C_4$ alkyl substituted $C_5$-$C_6$ cycloalkyl, phenyl, alkyl substituted phenyl of the general formula, $(R^6)_bPh$-, wherein Ph is phenylene, R6 is $C_1$-$C_{18}$ alkyl and b is an integer of from 1 to 3, phen ($C_1$-$C_{18}$) alkyl and $C_1$-$C_{18}$ alkyl substituted phen ($C_1$-$C_{18}$) alkyl having a total of from 7 to about 28 carbon atoms, $R'''$ is the substituted ethylene group, $-CH_2-CH(R'''')-$, wherein $R''''$ is selected from hydrogen, methyl and ethyl, and n is a number from 0 to 40, provided that when $R_5$ is phenyl or alkyl substituted phenyl, n is at least 1, which comprises heating said haloformate for a time and at temperatures sufficient to convert the haloformate to the corresponding halide in the presence of a catalytic amount of an organic quaternary salt catalyst represented by the general formula, $(Y_aH_{(4-a)})M^+X^-$, where M is nitrogen or phosphorus, X is a monovalent anion selected from the group consisting of halide ion, hydrogen sulfate anion and dihydrogen phosphate anion, a is 4, and Y is a monovalent alkyl group containing from 1 to 25 carbon atoms.

2. The method of claim 1 wherein the organic haloformate is an organic chloroformate and the corresponding halide is a chloride.

3. The method of claim 2 wherein conversion of the organic chloroformate to the corresponding organic chloride is conducted in the absence of a solvent for the chloroformate.

4. The method of claim 2 wherein the catalyst is selected from group represented by the general formulae, $(R_1,R_2,R_3,R_4N)^+X^-$ and $(R_1,R_2,R_3,R_4P)^+X'^-$, wherein $R_1$, $R_2$, $R_3$ and $R_4$ are each alkyl groups having from 1 to about 25 carbon atoms, X is a monovalent anion selected from the group consisting of halide ion, hydrogen sulfate anion and dihydrogen phosphate anion, and X' is a halide ion.

5. The method of claim 4 wherein the total number of carbon atoms in the groups $R_1$, $R_2$, $R_3$ and $R_4$ is from about 12 to about 35.

6. The method of claim 4 wherein the temperature at which the conversion is performed is from about 90° C. to about 150° C.

7. The method of claim 4 wherein the amount of catalyst used varies from 0.05 1.0 weight percent, based on the weight of the haloformate.

8. The method of claim 7 wherein the temperature at which the conversion is performed is from about 90° C. to about 150° C.

9. The method of claim 1 wherein the organic haloformate is represented by the general formula $R_5(OR''')_nOC(O)X$, wherein $R_5$ is a $C_1$-$C_{30}$ alkyl, X is chlorine and $R'''$ is the ethylene group, $-CH_2-CH_2-$, and n is a number form 0 to 40.

10. The method of claim 9 wherein the catalyst is selected from groups represented by the general formulae, $(R_1,R_2,R_3,R_4,N)^+X^-$ and $(R_1,R_2,R_3,R_4P)^+X'^-$, wherein $R_1$, $R_2$, $R_3$ and $R_4$ are each alkyl groups having from 1 to about 25 carbon atoms, X is a monovalent anion selected from the group consisting of halide ion, hydrogen sulfate anion and dihydrogen phosphate anion, and $X'$ is a halide ion.

11. The method of claim 10 wherein $R_5$ is a $C_8$-$C_{18}$ alkyl and n is a number from 2 to 20.

12. The method of claim 10 wherein the amount of catalyst used varies from 0.05 to about 1.0 weight percent, based on the weight of the haloformate.

13. The method of claim 12 wherein conversion of the organic haloformate to the correspond organic halide is conducted in the absence of a solvent for the haloformate.

14. The method of claim 12 wherein the temperature at which the conversion is performed is from about 90° C. to about 150° C.

15. The method of claim 12 wherein the catalyst is selected from alkyl trimethyl ammonium or phosphonium halides, dialkyl dimethyl ammonium or phosphonium halides, trialkyl methyl ammonium or phosphonium halides, and tetralkyl ammonium or phosphonium halides, wherein each of the alkyl groups contain from 8 to 18 carbon atoms and the halide is the chloride or the bromide.

16. The method of claim 14 wherein the catalyst is tetrabutyl ammonium bromide, or tetrabutyl ammonium hydrogen sulfate.

17. The method of claim 11 wherein the temperaturde at which the conversion is performed is from about 90° C. to about 150° C., the amount of a catalyst used is from 0.05 to about 1.0 weight percent, based on the weight of the haloformate, and the conversion is conducted in the absence of a solvent for the haloformate.

18. The method for preparing the corresponding chloride derivative of an organic chloroformate represented by the generaly formula, $R_5(OR''')_nOC(O)Cl$, wherein $R_5$ is a $C_1$—$C_{30}$ alkyl and $R'''$ is the ethylene group, $-CH_2CH_2-$, and n is a number from 0 to 40, which comprises:

a. reacting phosgene with a mixture of the corresponding alcohol, $R_5(OR''')_nOH$, and liquid organic quaternary salt catalyst represented by the general formula, $(R_1,R_2, R_3, R_4N)^+X^-$ and $(R_1,R_2,R_3,R_4P)^+X'^-$ where $R_1,R_2, R_3$ and $R_4$ are each $C_1$-$C_{25}$ alkyl, thereby to form the said organic chloroformate, and b. heating the organic chloroformate in the presence of a catalytic amount of said catalyst and in the absence of a solvent for the organic chloroformate at tempeatures of from about 90° C. to about 150° C. for a time suficient to convert the organic chloroformate to its corresponding organic chloride.

19. The method of claim 18 wherein from 0.05 to about 1.0 weight percent, based on the chloroformate, of the catlyst is used to catalyze the conversion of the organic chlorofromate to the corresponding organic chloride.

* * * * *

UNITED STATES PATENT AND TRADEMARK OFFICE
CERTIFICATE OF CORRECTION

PATENT NO. : 4,814,524

DATED : March 21, 1989

INVENTOR(S) : Robert G. Briody and James A. Manner

It is certified that error appears in the above-identified patent and that said Letters Patent is hereby corrected as shown below:

Claim 1, column 12, line 23, $(R^6)_b$ should be $(R_6)_b$;

Line 24, $R6$ should be $R_6$.

Claim 7, column 12, line 64, after "0.05" insert --to about--.

Claim 13, column 13, line 21, "correspond" should be --corresponding--.

Claim 17, column 14, line 4, "temperaturde" should be --temperature--.

Claim 18, column 14, line 12, "generaly" should be --general--.

Signed and Sealed this

Thirtieth Day of April, 1991

Attest:

HARRY F. MANBECK, JR.

Attesting Officer

Commissioner of Patents and Trademarks